US012669488B2

(12) United States Patent
Kang et al.

(10) Patent No.: US 12,669,488 B2
(45) Date of Patent: Jun. 30, 2026

(54) GAS DETECTOR WITH THERMAL DISSIPATION

(71) Applicant: Hand Held Products, Inc., Charlotte, NC (US)

(72) Inventors: SungSoo Kang, Seoul (KR); Dongil Ko, Seoul (KR); SangSu Park, Guri (KR); KiHo Bang, Gyeonggi-do (KR)

(73) Assignee: Hand Held Products, Inc., Charlotte, NC (US)

( * ) Notice: Subject to any disclaimer, the term of this patent is extended or adjusted under 35 U.S.C. 154(b) by 282 days.

(21) Appl. No.: 18/235,423

(22) Filed: Aug. 18, 2023

(65) Prior Publication Data

US 2025/0060347 A1 Feb. 20, 2025

(51) Int. Cl.
| | |
|---|---|
| *H05K 7/20* | (2006.01) |
| *G01N 33/00* | (2006.01) |
| *G01N 33/22* | (2006.01) |
| *G01N 37/00* | (2006.01) |

(52) U.S. Cl.
CPC ..... *G01N 33/0063* (2013.01); *G01N 33/0057* (2013.01); *G01N 33/0062* (2013.01); *H05K 7/20963* (2013.01); *G01N 2201/0236* (2013.01)

(58) Field of Classification Search
CPC ........... G01N 33/0009; G01N 33/0027; G01N 33/0036; G01N 33/0057; G01N 33/0062; G01N 2201/0236; H05K 7/20963
See application file for complete search history.

(56) References Cited

U.S. PATENT DOCUMENTS

| | | | | |
|---|---|---|---|---|
| 4,352,099 A | * | 9/1982 | Christen | ............ G01N 33/0009 422/96 |
| 5,060,114 A | * | 10/1991 | Feinberg | ............... H01L 23/552 257/E23.09 |
| 2010/0258331 A1 | * | 10/2010 | Dahlgren | ............... G01D 11/24 174/50.54 |
| 2017/0235385 A1 | * | 8/2017 | Park | ........................ G06F 3/046 345/174 |
| 2018/0007181 A1 | | 1/2018 | Lee et al. | |

FOREIGN PATENT DOCUMENTS

| | | |
|---|---|---|
| CN | 115361816 A | 11/2022 |
| CN | 217846035 U | 11/2022 |
| CN | 115472082 A | 12/2022 |
| WO | 2015/036725 A1 | 3/2015 |

OTHER PUBLICATIONS

Extended European Search Report Mailed on Dec. 23, 2024 for EP Application No. 24192289, 9 page(s).
CA Office Action Mailed on Sep. 8, 2025 for CA Application No. 3251621, 4 page(s).

* cited by examiner

*Primary Examiner* — Herbert K Roberts
(74) *Attorney, Agent, or Firm* — Alston & Bird LLP

(57) ABSTRACT

A gas detector is provided. The gas detector has a housing defining a cavity and a display module is disposed within the cavity. The display module has a first PCB, a base plate, a metal enclosure, and a thermal gap pad. The metal enclosure is positioned on top of the base plate, and the thermal gap pad is disposed in between the metal enclosure and the second PCB. The second PCB is disposed on top of the thermal gap pad.

20 Claims, 7 Drawing Sheets

104

100 →

104

108

502

504

506

GAS DETECTOR WITH THERMAL DISSIPATION

TECHNOLOGICAL FIELD

Example embodiments of the present disclosure relate generally to explosion proof gas detectors and more particularly to gas detectors having thermal dissipation during operation.

BACKGROUND

In order to prevent explosion of a combustible gas after reaching a certain concentration to ensure safety of production, a combustible gas detecting and alerting device is usually arranged in a factory or facility wherein a combustible gas is produced and used. A major constituent part of such combustible gas detecting and alerting device is a combustible gas detector. Current combustible gas detectors are mainly consisted of a gas sensitive element, a gas sensitive element fixing sleeve, a rain cover, and a cable entry means.

Currently, a combustible gas detector of such a structure is not secure in substance, thus, when applied in a combustible gas environment, there is a risk of detonating the surrounding environment, and more severe demand on explosion proof often cannot be satisfied. Thus, explosion-proof encapsulation is required. A traditional explosion-proof encapsulation manner of a combustible gas detector is to encapsulate a catalytic bead in a stainless-steel casing which has a flame catching and extinguishing sintered sheet, and the end of the casing is poured with epoxy to be leakage-proof. In accordance with the standard of explosion-proof authentication in Europe and North America, it is required that for any explosion-proof casing, if sealed by using a sealant, a bonding length between the sealant and the casing in the sealing direction shall be no less than 3 mm. Besides, the design of sealing with a sealant requires a sufficient size so that the explosion proof effect can be ensured. Thus, the size of a traditional design is usually large, and a small and portable combustible gas detector cannot be realized.

Usually, measurement means of a combustible gas detector include: a thermal conductivity detector, an infrared detector, and catalytic combustion detection, etc., these detection means mostly adopt the manner of heat measurement, that is, detecting a combustible gas by influence on the temperature or heat of a sensitive element caused by flow, infrared absorption, or combustion of a combustible gas. However, according to common knowledge, any detection involving heat measurement will necessarily be influenced by a change in temperature of the ambient environment. Thus, a heat-measuring sensor usually requires a reference detector or a reference element for canceling influence on the measurement of the detecting element caused by environmental factors such as temperature, humidity, pressure and airflow etc. The reference element needs to be infinitely consistent with the detecting element in term of several factors such as temperature, humidity, pressure, and airflow, etc., such that a maximal compensation effect can be achieved. Unfortunately, the compensation effect of reference elements in current combustible gas detectors, especially catalytic combustion or thermal conductivity sensors, are far from ideal due to the product design and the less advanced production process. That is to say, currently, combustible gas detectors manufactured by most of the manufacturers still have significant effects of temperature, humidity, pressure and airflow etc. although undergoing compensation by a reference element.

Existing explosion proof gas detectors have a metal enclosure, and a display module that allows an operator to configure a gas detector by showing device status. The display module has an LCD display, a PCB, and electrical components enveloped by plastic covers. During operation of the gas detectors, electrical components of the gas detectors generate heat, and the metal enclosure aids in maintaining inside temperature of the gas detector to secure the device performance. With such a metal enclosure, the heat stays inside the device and is not dissipated outside.

BRIEF SUMMARY

The illustrative embodiments of the present disclosure relate to a gas detector configured to dissipate heat. The gas detector has a housing defining a cavity, the housing has a top part and a bottom part, the top part coupled to the bottom part, and a display module. The display module is positioned within the cavity of the housing, and the display module has a first PCB, a second PCB, a base plate, a metal enclosure, and a thermal gap pad. The metal enclosure is positioned on top of the base plate, and the thermal gap pad is disposed in between the metal enclosure and the second PCB, wherein the second PCB is positioned in between the first PCB and the thermal gap pad.

In an example embodiment, the display module has an LCD display, and the LCD display is positioned on top of the first PCB.

In an example embodiment, an outer surface of the top part has a threaded part, and the inner portion of the bottom part has a threaded surface.

In an example embodiment, the bottom part has a display module support to receive the display module, wherein the display module support is in contact with the base plate of the display module.

In an example embodiment, the display module support has a contact metal plate in contact with the base plate of the display module.

In an example embodiment, wherein a diameter of the metal enclosure in in the range of 103 millimeter to 108 mm.

In an example embodiment, a display module comprises a first PCB, a second PCB, a base plate, a metal enclosure, and a thermal gap pad, wherein the metal enclosure is positioned on top of the base plate, and the thermal gap pad is disposed in between the metal enclosure and the second PCB, wherein the second PCB is positioned in between the first PCB and the thermal gap pad.

In an example embodiment, the display module further comprises an LCD display, wherein the LCD display is positioned on top of the first PCB.

In some embodiments, a diameter of the metal enclosure in in the range of 103 millimeter (mm) to 108 mm.

In an example embodiment, a length of the thermal gap pad is in the range of 60 millimeter (mm) to 80 mm.

In some embodiments, a gas detector comprises a housing defining a cavity, a display module positioned within the cavity of the housing, the display module having a first PCB and a second PCB, a base plate, a metal enclosure, and a thermal gap pad. The metal enclosure is positioned on top of the base plate, and the thermal gap pad is disposed in between the metal enclosure and the second PCB. The second PCB is disposed on top of the thermal gap pad.

In an example embodiment, the first PCB is disposed on top of the second PCB, and a bottom surface of the first PCB abuts a top surface of the second PCB.

In an example embodiment, the display module has an LCD display, and the LCD display is positioned on top of the first PCB.

In an example embodiment, an outer surface of the top part has a threaded part and inner portion of the bottom part has a threaded surface.

In some embodiments, the bottom part has a display module support to receive the display module, and the display module support is in contact with the base plate of the display module.

In an example embodiment, wherein the display module support has contact metal plate in contact with the base plate of the display module.

In some embodiments, a diameter of the metal enclosure in the range of 103 millimeter to 108 mm.

In an embodiment, a gas detector has a third PCB disposed in proximity to a bottom surface of the first LCD.

The above summary is provided merely for purposes of summarizing some example embodiments to provide a basic understanding of some aspects of the disclosure. Accordingly, it will be appreciated that the above-described embodiments are merely examples and should not be construed to narrow the scope or spirit of the disclosure in any way. It will be appreciated that the scope of the disclosure encompasses many potential embodiments in addition to those here summarized, some of which will be further described below.

BRIEF DESCRIPTION OF THE DRAWINGS

The description of the illustrative embodiments can be read in conjunction with the accompanying figures. It will be appreciated that for simplicity and clarity of illustration, elements illustrated in the figures have not necessarily been drawn to scale. For example, the dimensions of some of the elements are exaggerated relative to other elements. Embodiments incorporating teachings of the present disclosure are shown and described with respect to the figures presented herein, in which:

FIG. 2(*b*) illustrates a sectional view of the display module, in accordance with an example embodiment of the present disclosure;

DETAILED DESCRIPTION

Figure 1:
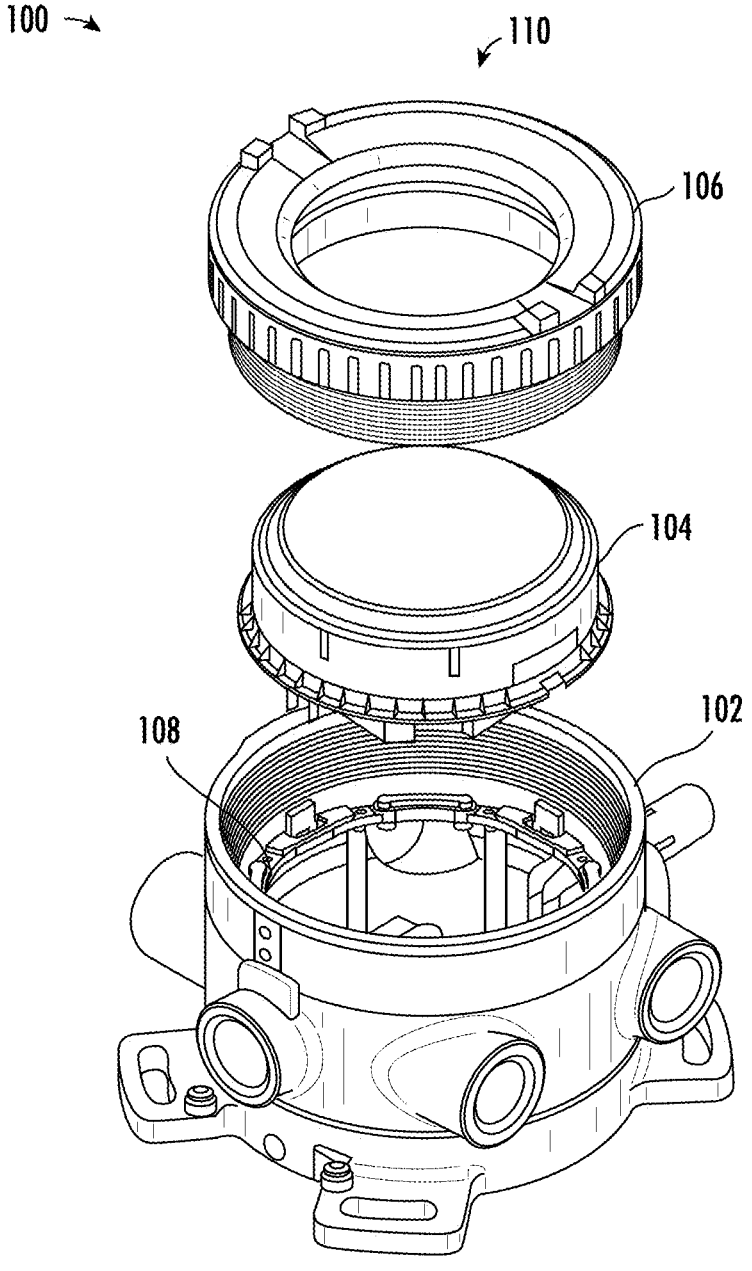
FIG. 1 illustrates an exploded view of a gas detector, in accordance with an example embodiment of the present disclosure.

Some embodiments of the present disclosure will now be described more fully hereinafter with reference to the accompanying drawings, in which some, but not all embodiments are shown. Indeed, the disclosure may be embodied in many different forms and should not be construed as limited to the embodiments set forth herein; rather, these embodiments are provided so that this disclosure will satisfy applicable legal requirements. The terms "or" and "optionally" are used herein in both the alternative and conjunctive sense, unless otherwise indicated. The terms "illustrative" and "exemplary" are used to be examples with no indication of quality level. Like numbers refer to like elements throughout.

In many working environments, explosion proof gas detectors are used for monitoring levels of gas in an environment and alerting users when levels of a monitored gas increases above a predefined threshold. The gas detectors have a display module for displaying operation status of the gas detectors and other information regarding the gas detector. An explosion proof gas detector has an explosion proof container, and electrical equipment of the gas detector are placed inside the explosion proof container. The explosion proof container is normally made of metal and has a fully enclosed structure. The explosion proof container is capable of withstanding high pressure and high temperature when gas or steam explosion occurs.

During operation of the gas detector, the electrical components, such as circuit boards, wirings continually generate heat within the gas detector. The heat so generated stays within the explosion proof container and fails to dissipate the heat to the outside environment. The circuit boards have components that have difficulty in operation when surrounding temperature is high. The heat, when exceeds beyond a predefined level, affects operation of the components of the circuit boards. To this end, some existing gas detectors having explosion proof enclosures are not efficient in dissipating heat generated inside the gas detector that affects operation of the electrical components of the gas detectors.

Various example embodiments described in present disclosure relates to an explosion proof gas detector having heat dissipation for emitting the generated heat out of the housing of the gas detector. The gas detector has a housing defining a cavity and a display module is placed within the cavity. The display module has an LCD display, a first PCB, a second PCB, a base plate, a metal enclosure, and a thermal gap pad. The metal enclosure is explosion proof and is positioned above the base plate, and the thermal gap pad is positioned above the metal enclosure such that a bottom surface of the thermal gap pad abuts a top surface of the metal enclosure. The second PCB is disposed in between the thermal gap pad and the first PCB. The first PCB is positioned close to the LCD display of the display module.

The details regarding components of the position sensor and their working are described in detail with reference to subsequent figures and description.

The components illustrated in the figures represent components that may or may not be present in various example embodiments described herein such that embodiments may include fewer or more components than those shown in the figures while not departing from the scope of the disclosure.

Turning now to the drawings, the detailed description set forth below in connection with the appended drawings is intended as a description of various example configurations and is not intended to represent the only configurations in which the concepts described herein may be practiced. The detailed description includes specific details for the purpose of providing a thorough understanding of various concepts with like numerals denoting like components throughout the several views. However, it will be apparent to those skilled in the art of the present disclosure that these concepts may be practiced without these specific details.

FIG. 1 is an exploded view of a gas detector 100, in accordance with an example embodiment of the present disclosure. The gas detector 100 is explosion proof and has a housing having a bottom part 102, a display module 104, and a top part 106. The gas detector 100 has a display module support assembly 108 disposed on an inner wall within a cavity of the bottom part 102. In an assembled state, the display module 104 is positioned over the display module support assembly 108 within the bottom part 102 and the top part 106 completely encases the display module 104. The top part 106 has a circular window 110 through which a user can view the display module 104 and read information displayed on the display module 104. In an example, the inner wall of the housing 103 has threaded surface and the outer wall of the top part 106 has threaded surface for coupling. In an example, the bottom part 102 and the top part 106 are coupled such that a user may disassemble and separate the top part 106 from the bottom part 102.

Figure 2A:
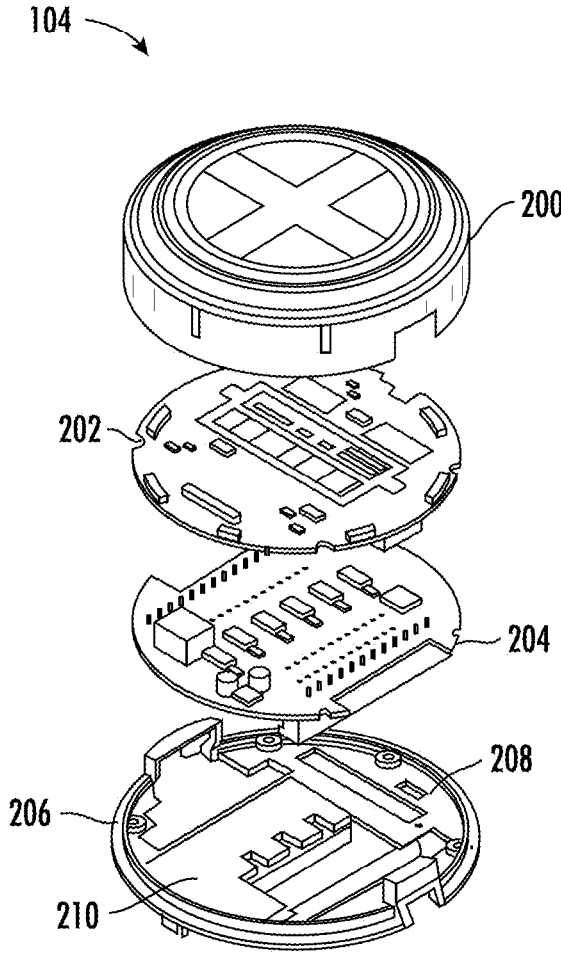
FIG. 2(*a*) is an exploded view of a display module, in accordance with an example embodiment of the present disclosure.
Figure 2B:
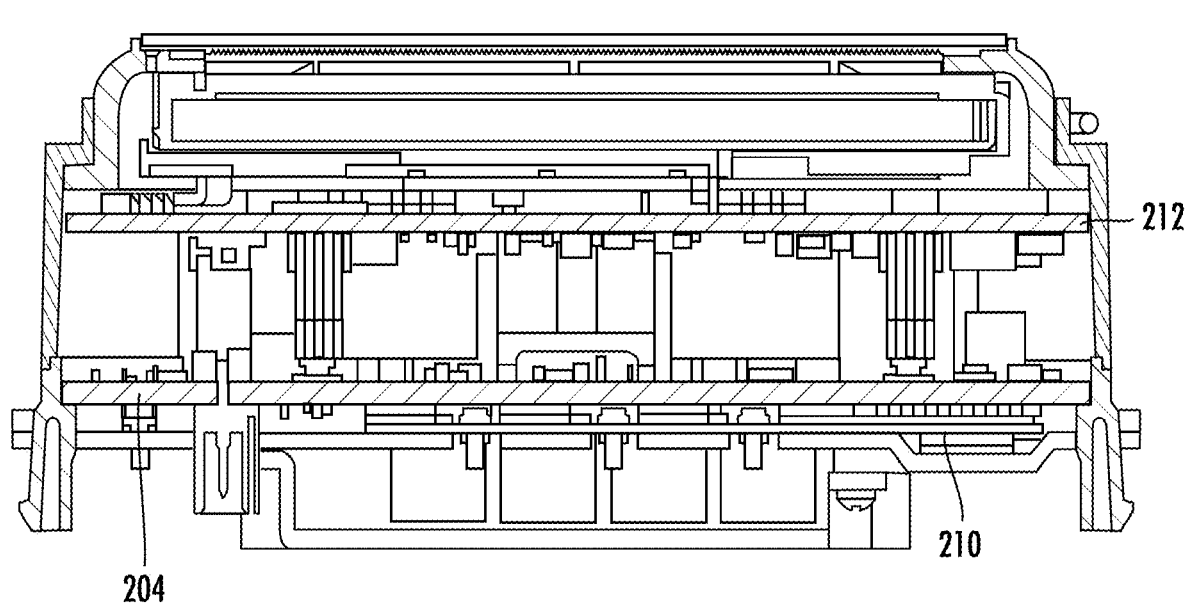

FIGS. 2(a) and 2(b) illustrate components of the display module 104, in accordance with an embodiment of the present disclosure. The display module 104 comprises a Liquid Crystal Display (LCD) 200, a first PCB 202, also referred to as a processor PCB, a second PCB 204, also referred to as a terminal PCB, a base plate 206, a metal enclosure 208, and a thermal gap pad 210. The display module 104 also has a third PCB 212, referred to as a heater PCB positioned in proximity to a bottom surface of the LCD 200. An operating temperature of the gas detector 100 is usually in between −55° C.-75° C. In an example, when operating in low temperatures, the heater PCB 212 is used for generating heat inside the display module 104 to protect components from low temperatures that affects performance of the components of the display module 104. In operating environments having moderate to high temperatures, the PCBs 202, 204, and the heater PCB 212 generate heat inside the display module 104 during operation which may increase the temperature to more than 75° C. Such high temperatures may affect the performance of the electrical components or damage the components of the display module 104 and the gas detector 100. The heat is not completely dissipated outside due to encapsulation of the PCBs, other components of the gas detector 100, and the display module 104 by the metal enclosure 208. Additionally, the bottom part 102 and the top part 106 are connected to each other through the threaded surface that does not provide any gap in between and prevent dissipation of heat.

Further, most of the heat generating components, such as isolator, transistor, relay, diodes, LDO are disposed in proximity to the second PCB 204 (or terminal PCB) bottom surface. In an example, the heat generating components are connected to the thermal gap pad 210 in between the heat PCB 212 and a bottom case disposed at a bottom surface of the display module 104, for dissipation of heat. The thermal gap pad 210 is placed in between the second PCB 204 and the bottom case of the display module 104. In addition, the bottom case, which is conventionally made of plastic material, is replaced with a metal case for improved heat dissipation.

Figure 3:
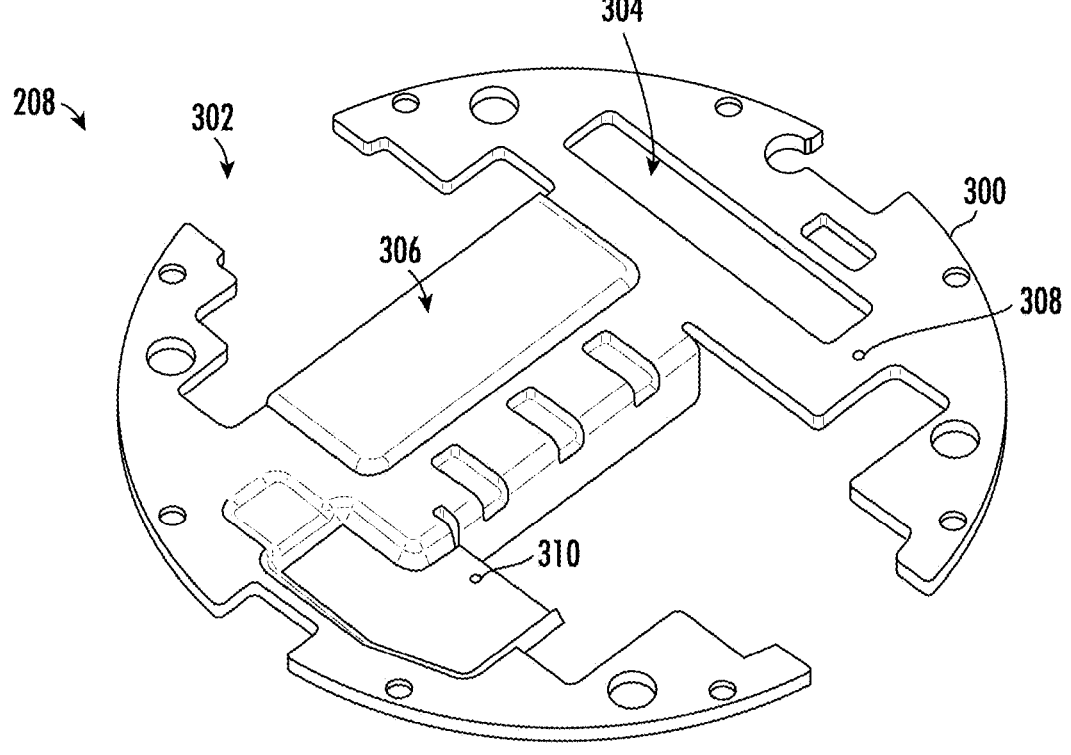
FIG. 3 illustrates a metal enclosure of a display module of a gas detector, in accordance with an example embodiment of the present disclosure.

The metal enclosure 208 is illustrated in FIG. 3, in accordance with an embodiment of the present disclosure. The metal enclosure 208 has a body 300 which is of a circular shape and is positioned in proximity to a bottom surface of the second PCB 204. As shown, the body 300 has few gaps, such as 302 and 304. The gaps 302 and 304 are to accommodate electrical components of different heights on the second PCB 204. The body 300 has a forming area 306 and few through hole 308, and 310 for coupling the metal enclosure 208 with the bottom surface of the display module 104. The forming area 306 reduces the gap from the PCB components such that a 1.5 t gap pad can be placed in between to contact the metal enclosure and the PCB components. In an example, the diameter of the body 300 is 105.00 millimeters (mm) (approx.). A width of the forming area 306 is around 22 mm approximate and the length is 54 mm (approx.), and the gap between the two through holes is around 64 mm (approx.).

In an example, the electrical components have different structures and height and can have different gaps between the metal enclosure 208 and the components. To have a uniform contact of the components with metal enclosure, a soft material with high thermal conductivity, referred to as the thermal gap pad 210, is placed in between the electrical components and the metal enclosure 208 for efficient heat dissipation.

Figure 4:
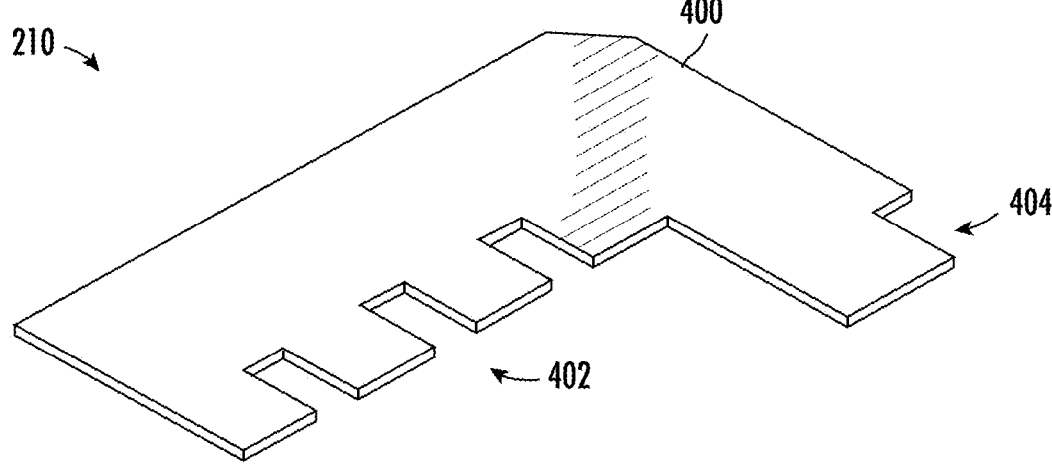
FIG. 4 illustrates a thermal gap pad of a display module of a gas detector, in accordance with an example embodiment of the present disclosure.

FIG. 4 illustrates the thermal gap pad 210, in accordance with an embodiment of the present disclosure. The thermal gap pad 210 is disposed in between the second PCB 204 and the bottom case. In an example, the thermal gap pad 210 is a soft and compliant gap filling material with a thermal conductivity of 3.0 W/m-K. The material offers thermal performance at low pressures due to a unique 3.0 W/m-K filler package and low modulus resin formulation. Such a material is ideal for applications requiring low stress on components and boards during assembly. The thermal gap pad 210 maintains a conformable nature that allows quick recovery and excellent wet-out characteristics, even to surfaces with high roughness and topography. The thermal gap pad 210 has a body 400 and few indents 402, and 404 to align with the metal enclosure 208 disposed below the thermal gap pad 210. In an example, length of the thermal gap pad 210 is in a range of around 60 mm to 80 mm, and width is around 50 mm and has a thickness of around 0.508 mm to 3.175 mm. An operating temperature range for the thermal gap pad 210 is from −60° C. to 200° C. Each of the indents 402 have a length of around 5 mm each and width of 10 mm each and length of indent 404 is around 10 mm. In an example, the thermal gap pad 210 is made from silicone polymer that is combined with a thermal medium (usually ceramic). During manufacturing of the thermal gap pad 210, the silicone and ceramic powders are mixed, cast and cured to a soft, conformal thermal pad material, in a sheet form. In an example, the thermal gap pad 210 has fiberglass as a reinforcement carrier.

Figure 5A:
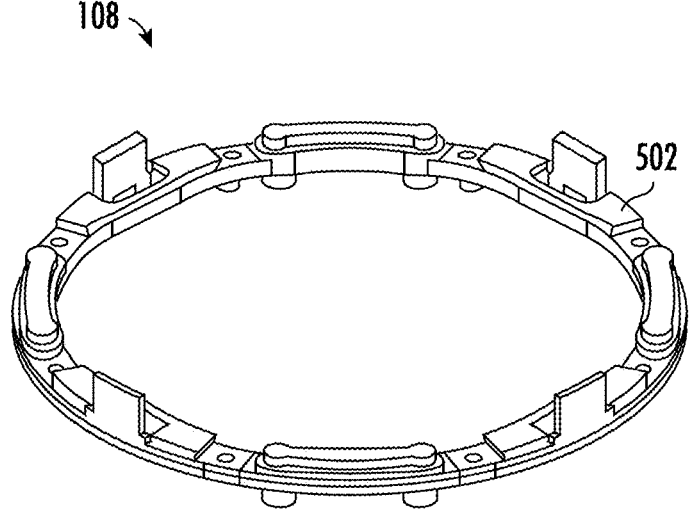
FIGS. 5(*a*) and 5(*b*) illustrate various views of a contact metal plate of a gas detector, in accordance with an example embodiment of the present disclosure.
Figure 5B:
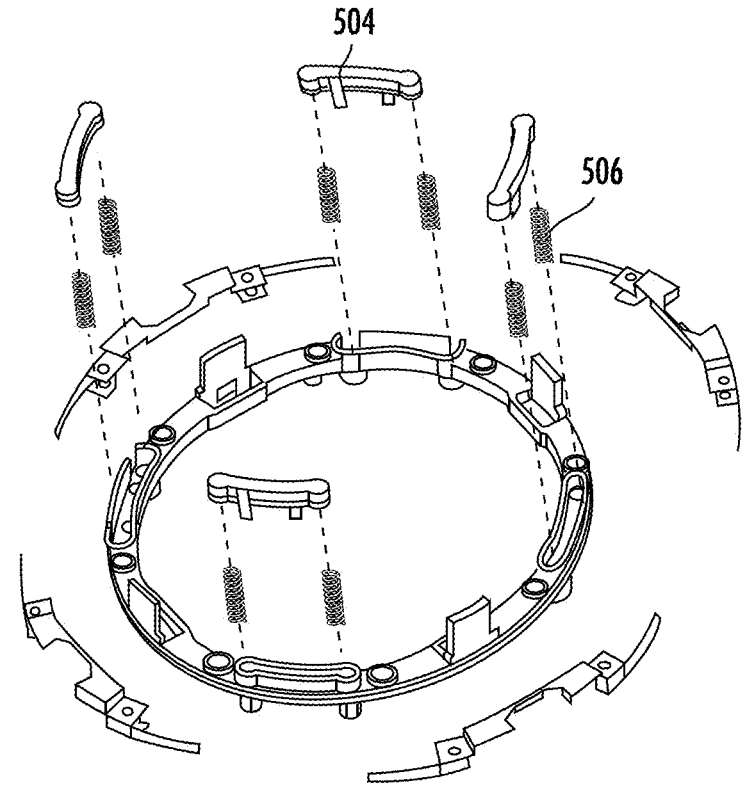

Referring to FIGS. 5(a) and 5(b), various views of the display module support assembly 108 are illustrated, in accordance with an embodiment of the present disclosure. The display module support assembly 108 has contact metal plate 502 as a subpart, support portions 504, and spring pieces 506. In an example, the support portions 504 are made of metal. The contact metal plate 502 and support portions 504 provide support to the display module 104 when the display module 104 is disposed on inner wall of the bottom part 102. The support portions 504 and spring pieces 506 push display module 104 to contact to the glass of transmitter enclosure top 106. This allows fixing the position of the display module 104 against movement or vibration. Further, the support portions 504 renders the display module 104 in floating at the same time. The contact metal plate 502 contacts to the metal enclosure of display module 104. In an example, the display module support assembly 108 and a bottom surface of the display module 104 are aligned such that the metal enclosure 208 and the support portions 504 are in direct contact with each other. The contact of the metal enclosure 208 and the support portions 504 allows direct transfer of the heat from the metal enclosure 208 to the support portions 504. The springs 506 provide optimal support to the display module 104 to withstand vibrations. Further, the contact metal plate 502 is made of phosphor bronze C5210H. The contact metal plate 502 is a folded sheet metal that operates as a spring and stays connected with the display module 104 based on the tension created by the spring. A side wing shape of the contact metal plate 502 contacts an inner side wall of transmitter enclosure bottom part 102 for heat dissipation by conduction.

Figure 6:
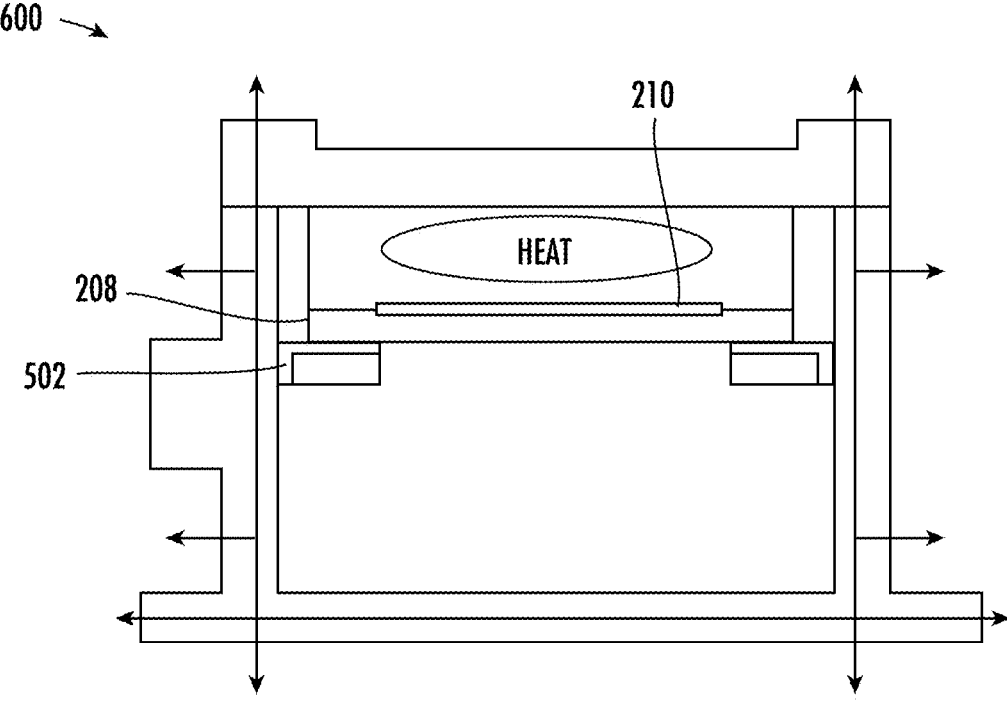
FIG. 6 illustrates flow of heat in a gas detector during operation of the gas detector, in accordance with an example embodiment of the present disclosure.

FIG. 6 illustrates flow of heat within the gas detector 100, from the first PCB 202 to the bottom part 102 of the gas detector 100, in accordance with an embodiment for the present disclosure. The overall objective is to direct the heat generated inside the PCBs, such as the PCB 202 to the bottom part 102 and then dissipate the heat to the outside environment from the bottom part 102. In an example, a fan (not shown in the figure) is attached to the bottom case to extract the heat generated in the PCBs and draw the heat to the bottom part 102 of the display module 104. The arrows in FIG. 6 indicate direction of flow of heat.

As shown, heat is generated by the electrical components, such as PCB 202, PCB 204 and the heater PCB 212 within the display module 104, the heat generated by the electrical components is absorbed by the thermal gap pad 210 and then the heat is transferred to the metal enclosure 208 from the thermal gap pad 210. The metal enclosure 208 is in contact with the support portions 504 of the display module support assembly 108. The heat is then transferred to the display module support assembly 108. The display module support assembly 108 is in surface contact with the metal of the bottom part 102. Heat is then transferred to the metal body of the bottom part 102 and then transferred to the outside environment through the metal body of the bottom part 102.

In another example, the display module support assembly 108 is disposed on an inner wall of the bottom part 102 and the bottom surface of the display module 104 is in contact with the display module support assembly 108, such that heat generated inside the display module 104 is transferred from the bottom surface of the display module 104 of the display module 104 to the display module support assembly 108 and then dissipated to the outside environment through the bottom part 102. In an example, the components for heat dissipation are accommodated in the housing without occupying any extra space or increasing the size of the gas detector 100. The invention provides an advantage of improved heat dissipation without increase in the footprint or size of the gas detector 100 or the display module 104.

References within the specification to "one embodiment," "an embodiment," "embodiments", or "one or more embodiments" are intended to indicate that a particular feature, structure, or characteristic described in connection with the embodiment is included in at least one embodiment of the present disclosure. The appearance of such phrases in various places within the specification are not necessarily all referring to the same embodiment, nor are separate or alternative embodiments mutually exclusive of other embodiments. Further, various features are described which may be exhibited by some embodiments and not by others. Similarly, various requirements are described which may be requirements for some embodiments, but not other embodiments.

It should be noted that, when employed in the present disclosure, the terms "comprises," "comprising," and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

As required, detailed embodiments of the present disclosure are disclosed herein; however, it is to be understood that the disclosed embodiments are merely exemplary, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

While it is apparent that the illustrative embodiments herein disclosed fulfill the objectives stated above, it will be appreciated that numerous modifications and other embodiments may be devised by one of ordinary skill in the art. Accordingly, it will be understood that the appended claims are intended to cover all such modifications and embodiments, which come within the spirit and scope of the present disclosure.

What is claimed is:

1. A gas detector comprising:
   a housing defining a cavity, the housing comprising a top part and a bottom part, the top part coupled to the bottom part; and
   a display module positioned within the cavity of the housing, the display module comprising:
      a first PCB and a second PCB, each generating heat in response to operation of the display module;
      a base plate;
      a metal enclosure; and
      a thermal gap pad, wherein the metal enclosure is positioned on top of the base plate, and the thermal gap pad is disposed in between the metal enclosure and the second PCB, wherein the second PCB is positioned in between the first PCB and the thermal gap pad,
      wherein the display module is received by a display module support disposed on the bottom part of the housing, the display module support comprising a contact metal plate and support portions,
      wherein the metal enclosure is in contact with the contact metal plate and the support portions, wherein the contact allows direct transfer of heat from the metal enclosure to the support portions and the contact metal plate.

2. The gas detector of claim 1, wherein the display module further comprises an LCD display, and the LCD display is positioned on top of the first PCB.

3. The gas detector of claim 1, wherein an outer surface of the top part has a threaded part, and an inner portion of the bottom part has a threaded surface.

4. The gas detector of claim 1, wherein the bottom part has the display module support to receive the display module, wherein the display module support is in contact with the base plate of the display module.

5. The gas detector of claim 3, wherein the display module support has the contact metal plate in contact with the base plate of the display module.

6. The gas detector of claim 1, wherein a diameter of the metal enclosure is in the range of 103 millimeter to 108 mm.

7. A display module comprising:
   a first PCB and a second PCB, each generating heat in response to operation of the display module;
   a base plate; and
   a metal enclosure; and

US 12,669,488 B2

9 a thermal gap pad, wherein the metal enclosure is positioned on top of the base plate, and the thermal gap pad is disposed in between the metal enclosure and the second PCB, wherein the second PCB is positioned in between the first PCB and the thermal gap pad wherein the first PCB, the second PCB, and the base plate are received on a display module support, the display module support comprising a contact metal plate and support portions, wherein the metal enclosure is in contact with the contact metal plate and the support portions, wherein the contact allows direct transfer of heat from the metal enclosure to the support portions and the contact metal plate.

8. The display module of claim 7, wherein the display module further comprises an LCD display, wherein the LCD display is positioned on top of the first PCB.

9. The display module of claim 7, wherein a diameter of the metal enclosure is in the range of 103 millimeter (mm) to 108 mm.

10. The display module of claim 7, wherein a length of the thermal gap pad is in the range of 60 millimeter (mm) to 80 mm.

11. The display module of claim 8, further comprising a third PCB, disposed in proximity to a bottom surface of the LCD display.

12. The display module of claim 7, wherein the thermal gap pad is made of silicone and ceramic powder.

13. A gas detector comprising:
a housing defining a cavity; and
a display module positioned within the cavity of the housing, the display module comprising:
a first PCB and a second PCB, each generating heat in response to operation of the display module;
a base plate;
a metal enclosure; and
a thermal gap pad, wherein the metal enclosure is positioned on top of the base plate, and the thermal gap pad is disposed in between the metal enclosure and the second PCB, wherein the second PCB is disposed on top of the thermal gap pad, wherein the display module is received by a display module support disposed on a bottom part of the housing, the display module support comprising a contact metal plate and support portions, wherein the metal enclosure is in contact with the contact metal plate and the support portions, wherein the contact allows direct transfer of heat from the metal enclosure to the support portions and the contact metal plate.

14. The gas detector of claim 13, wherein the first PCB is disposed on top of the second PCB, and a bottom surface of the first PCB abuts a top surface of the second PCB.

15. The gas detector of claim 13, wherein the display module further comprises an LCD display, and the LCD display is positioned on top of the first PCB.

16. The gas detector of claim 13, the housing having a top part and a bottom part, wherein an outer surface of the top part has a threaded part, and an inner portion of the bottom part has a threaded surface.

17. The gas detector of claim 16, wherein the bottom part has the display module support to receive the display module, wherein the display module support abuts the base plate of the display module.

18. The gas detector of claim 13, wherein the display module support has the contact metal plate in contact with the base plate of the display module.

19. The gas detector of claim 13, wherein a diameter of the metal enclosure is in the range of 103 millimeter to 108 mm.

20. The gas detector of claim 15, further comprising a third PCB, disposed in proximity to a bottom surface of the LCD display.

* * * * *